(12) United States Patent
Yasuno et al.

(10) Patent No.: US 10,551,348 B2
(45) Date of Patent: Feb. 4, 2020

(54) ION MOBILITY SPECTROMETER

(71) Applicant: SHIMADZU CORPORATION, Kyoto-shi, Kyoto (JP)

(72) Inventors: Motohide Yasuno, Kyoto (JP); Ryo Fujita, Manchester (GB)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/527,192

(22) PCT Filed: Nov. 17, 2014

(86) PCT No.: PCT/JP2014/080318
§ 371 (c)(1),
(2) Date: May 16, 2017

(87) PCT Pub. No.: WO2016/079780
PCT Pub. Date: May 26, 2016

(65) Prior Publication Data
US 2017/0328863 A1 Nov. 16, 2017

(51) Int. Cl.
*G01N 27/62* (2006.01)
*H01T 19/00* (2006.01)
(Continued)

(52) U.S. Cl.
CPC ......... *G01N 27/622* (2013.01); *G01N 30/724* (2013.01); *H01J 49/045* (2013.01); *H01J 49/0445* (2013.01); *H01J 49/145* (2013.01)

(58) Field of Classification Search
CPC .............................. G01N 27/622; H01T 19/00
See application file for complete search history.

(56) References Cited

U.S. PATENT DOCUMENTS 3,845,301 A    10/1974  Wernlund et al.
4,260,884 A *   4/1981  Lovelock ............... H01T 19/00
                                                            250/324
(Continued)

FOREIGN PATENT DOCUMENTS

CA    1 171 463 A    7/1984
EP    0 026 683 A2   4/1981
(Continued)

OTHER PUBLICATIONS

Written Opinion dated Dec. 16, 2014 in application No. PCT/JP2014/080318.
(Continued)

*Primary Examiner* — Nicole M Ippolito
*Assistant Examiner* — Sean M Luck
(74) *Attorney, Agent, or Firm* — Sughrue Mion, PLLC

(57) ABSTRACT

A spray area in which a large number of droplets of a liquid sample sprayed from a spray nozzle is separated from the tip of a needle electrode for corona discharge by a sufficiently large distance, with a grid electrode facing the needle electrode placed in between. Ring electrodes for creating an electric field which drives primary ions that should react with the sample and generate sample-derived ions are provided within an ion chamber between the grid electrode and the spray area. Primary ions generated by corona discharge within the space between the needle electrode and the grid electrode pass through the opening of the grid electrode, reach the spray area under the effect of the electric field, and ionize sample components. Since the droplets are prevented from adhering to the needle electrode, the corona discharge is maintained in a stable state.

8 Claims, 5 Drawing Sheets

(51) Int. Cl.
*G01N 30/72* (2006.01)
*H01J 49/04* (2006.01)
*H01J 49/14* (2006.01)

(56) References Cited

U.S. PATENT DOCUMENTS

| | | | |
|---|---|---|---|
| 4,390,784 A | 6/1983 | Browning et al. | |
| 5,726,447 A * | 3/1998 | Aisawa | H01J 49/145 250/288 |
| 5,998,215 A * | 12/1999 | Prather | H01J 49/0445 250/281 |
| 6,349,668 B1 * | 2/2002 | Sun | B05B 5/00 118/723 E |
| 8,653,449 B2 | 2/2014 | Denton et al. | |
| 2002/0017605 A1 * | 2/2002 | Jenkins | G01N 27/622 250/287 |
| 2004/0089802 A1 * | 5/2004 | Kato | H01J 49/107 250/285 |
| 2011/0036977 A1 | 2/2011 | Denton | |
| 2012/0120395 A1 * | 5/2012 | Hahn | G01J 3/0286 356/326 |
| 2014/0151545 A1 | 6/2014 | Denton et al. | |

FOREIGN PATENT DOCUMENTS

| | | |
|---|---|---|
| EP | 2 218 092 | 3/2013 |
| JP | 11-304761 A | 11/1999 |
| JP | 2005-174619 A | 6/2005 |
| JP | 3819146 B2 | 9/2006 |
| JP | 2009-002815 A | 1/2009 |
| JP | 2009524036 A | 6/2009 |
| JP | 2011-503805 A | 1/2011 |
| JP | 5425798 B2 | 2/2014 |
| WO | 2005/059539 A1 | 6/2005 |
| WO | 2009/094059 A3 | 7/2009 |

OTHER PUBLICATIONS

International Search Report for PCT/JP2014/080318 dated Dec. 16, 2014 [PCT/ISA/210].
Written Opinion for PCT/JP2014/080318 dated Dec. 16, 2014 [PCT/ISA/237].

* cited by examiner

ION MOBILITY SPECTROMETER

CROSS REFERENCE TO RELATED APPLICATIONS

This application is a National Stage of International Application No. PCT/JP2014/080318 filed Nov. 17, 2014, the contents of all of which are incorporated herein by reference in their entirety.

TECHNICAL FIELD

The present invention relates to an ion mobility spectrometer, and more specifically, to an ion mobility spectrometer provided with an atmospheric pressure ion source, for producing ions from a compound in a liquid sample in an ambience of atmospheric pressure and for analyzing the ions using an ion mobility.

BACKGROUND ART

When an ion produced from a compound in a sample is made to move in a gas medium (or liquid medium) by the effect of an electric field, the ion moves at a speed proportional to the mobility which is determined by the strength of the electric field, size of the ion and other factors. Ion mobility spectrometry is a measurement method utilizing this ion mobility for an analysis of a compound. Analyzing devices employing this measurement method are generally called the "ion mobility spectrometer", "ion mobility meter" or otherwise. In the following description, an ion mobility spectrometer is referred to as an "IMS device".

Commonly used IMS devices include an ion source for ionizing compound molecules in a sample, a drift region formed within a housing having a cylindrical form (or other appropriate forms) for separating ions according to their ion mobility, and a detector for detecting the ions which have travelled through the drift region (for example, see Patent Literature 1). Normally, a uniform electric field which exhibits a downward potential gradient in the direction in which the ion travels (ion-moving direction), i.e. which has the effect of accelerating the ions, is formed within the drift region. Additionally, a stream of neutral gas (which is normally an inert gas) is formed in the opposite direction to the accelerating direction by the electric field, i.e. the ion-moving direction.

The ions produced in the ion source and introduced into the drift region travel along the downward potential gradient while colliding with the neutral gas flowing in the opposite direction. During this movement, the ions are temporally separated according to their ion mobility which depends on the size, three-dimensional structure, electric charge and other properties of the ions. Ions having different ion mobilities reach the detector having certain intervals of time. If the electric field within the drift region is uniform, it is possible to calculate the collision cross-section between an ion and the neutral gas based on the drift time required for the ion to pass through the drift region.

In the case of analyzing a compound in a gas sample using an IMS device, an ion source which ionizes the compound using beta rays emitted from a radioactive isotope, such as $^{63}Ni$, or an atmospheric pressure ion source which uses corona discharge, or other types of ion sources are commonly used (see Patent Literatures 1 and 2). Such an IMS device can be used as a detector for a gas chromatograph (GC). A GC-IMS in which an IMS device is connected to the exit port of the column of a GC has been practically used. However, the range of substances that can be detected with GC-IMS is limited to volatile substances that can be vaporized in the sample injection section of the GC. Accordingly, in order to enable the detection of a wider range of substances inclusive of hard-to-volatile and non-volatile substances, an LC-IMS which uses an IMS device as the detector for a liquid chromatograph (LC) has been developed.

In the LC-IMS, it is necessary to produce gas-phase ions from a compound in a liquid sample in the ion source of the IMS device. For this purpose, an ion source which employs atmospheric pressure ionization is used, such as the atmospheric pressure chemical ionization (APCI), electrospray ionization (ESI) or atmospheric pressure photoionization (APPI), all of which are also commonly used in liquid chromatograph mass spectrometers (LS-MS).

CITATION LIST

Patent Literature

Patent Literature 1: JP 2005-174619 A
Patent Literature 2: JP 2009-2815 A

SUMMARY OF INVENTION

Technical Problem

In any of these atmospheric pressure ion sources, a liquid sample which contains a compound to be analyzed is sprayed into an ambience of atmospheric pressure so as to produce gaseous ions originating from the target compound while vaporizing the sample solvent, i.e. while promoting the desolvation. However, depending on the flow rate and/or solvent composition of the liquid sample, it may be difficult for the solvent to vaporize from the droplets formed by the spraying process. For example, organic solvents (e.g. acetonitrile) and water are commonly used as the mobile phase for an LC. Water has a higher boiling point than organic solvents. Therefore, if the mobile phase has a considerably high percentage of water, the desolvation does not progress efficiently.

In the LC-IMS, there is normally no pressure difference between the ion source and the drift region; actually, the neutral gas supplied in the opposite direction to the ion-moving direction within the drift region gently overflows from the drift region toward the ion source. Therefore, the droplets formed by the spraying process in the ion source tend to stay within the ion source.

For example, in the APCI ion source, when it is difficult for the solvent in the droplets to vaporize, the droplets formed by the spraying process become more likely to adhere to the needle electrode for corona discharge. The adhered droplets decrease the strength of the electric field around the tip of the needle electrode, making it difficult to maintain the corona discharge in a stable state. As a result, the ionization of the compound to be analyzed also becomes unstable, which causes a fluctuation in the intensity of the detected signal or a generation of spike noises, making the eventually obtained spectrum (ion mobility spectrum) or chromatogram less reliable. FIG. 9 is an example of the chromatogram observed with a conventional LC-APCI-IMS device in which spike noises are present.

Additionally, an LC-IMS device employing an atmospheric pressure ion source which uses nebulizer gas (which is not limited to the APCI ion source) has another problem, i.e. a considerable amount of baseline fluctuation occurring in the spectrum. FIG. 10 shows an example of the spectrum observed with a conventional LC-APCI-IMS device in which the baseline fluctuation is present.

The present invention has been developed to solve the previously described problems. Its first objective is to provide an ion mobility spectrometer capable of preventing, as thoroughly as possible, the adhesion of the droplets to the needle electrode for corona discharge so as to maintain a stable corona discharge and thereby enable a stable ionization even in the situation where the desolvation of the droplets formed by the spraying process in the APCI ion source does not easily progress.

The second objective of the present invention is to provide an ion mobility spectrometer using an atmospheric pressure ion source, the ion mobility spectrometer being capable of reducing the amount of baseline fluctuation occurring in the spectrum.

Solution to Problem

The ion mobility spectrometer according to the present invention developed for achieving the aforementioned first objective is an ion mobility spectrometer in which a component in a sample is ionized under substantially atmospheric pressure and the produced ions are made to enter and drift through a drift region maintained at substantially atmospheric pressure so as to separate the ions according to their ion mobility, the ion mobility spectrometer including:

a) a sample spray section for spraying a liquid sample into an ionization chamber maintained at substantially atmospheric pressure;

b) a needle electrode located within the ionization chamber on an opposite side to the drift region across a spray area into which the liquid sample is sprayed from the sample spray section, for inducing corona discharge to generate a primary ion for generating a sample-derived ion by reacting with a component in a sample sprayed from the sample spray section; and c) a primary-ion-driving electric field creator for creating, between the spray area and a primary ion generation area in which the primary ion is generated by corona discharge induced through the needle electrode, an electric field for driving the primary ion present within the primary ion generation area toward the spray area.

In the ion mobility spectrometer according to the present invention, a compound in a liquid sample is ionized by an APCI method. Within the ionization chamber, the spray area into which the liquid sample is sprayed from the sample spray section, i.e. the area in which a large number of sample droplets are present, is spatially separated from the needle electrode for inducing corona discharge for generating a primary ion. Therefore, even in the situation where the solvent cannot easily vaporize from the sample droplets formed by the spraying process from the sample spray section, the sample droplets will not adhere to the tip of the needle electrode. This enables the corona discharge to be maintained in a stable state. If the sample droplets, which are a dielectric material, were adhered to the tip of the needle electrode, the electric field at the needle tip would be weaker and the corona discharge would be unstable. Preventing an easy adhesion of the droplets enables the corona discharge to be maintained in a stable state. Consequently, the primary ion for ionizing the sample component will be generated in a stable manner.

The primary ion generated within the primary ion generation area around the tip of the needle electrode by corona discharge is transferred to the spray area under the effect of the electric field created by the primary-ion-driving electric field creator. Therefore, despite the spatial separation between the tip of the needle electrode and the spray area, a sufficient amount of primary ions for causing a reaction with the gas molecules of the target component generated from the droplets can be supplied to the spray area. Accordingly, a high level of ionization efficiency can be achieved.

As one specific mode of the ion mobility spectrometer according to the present invention, the primary-ion-driving electric field creator may include: a grid electrode facing the needle electrode, the grid electrode arranged so as to partition the space between the primary ion generation area and the spray area; and a voltage supplier for applying a predetermined DC voltage to the grid electrode.

In this configuration, the primary ions generated within the primary ion generation area by corona discharge move through the openings of the grid electrode into the spray area. Although some ions may come in contact with the grid elements (electrode elements) of the grid electrode and disappear, most of the primary ions can be efficiently introduced into the spray area, since the grid surface has a substantially uniform potential distribution, which reduces the disturbance of the equipotential surfaces in the electric field created within the space between the grid surface and the tip of the needle electrode. Additionally, the electrode included in the primary-ion-driving electric field creator doubles as the counter-electrode for the needle electrode to induce corona discharge. Using the flat grid electrode as this counter-electrode allows the distance between the tip of the needle electrode and the counter-electrode to be shortened. This enables a stable corona discharge to easily occur even at a lower voltage.

As another mode of the ion mobility spectrometer according to the present invention, the primary-ion-driving electric field creator may include: a ring electrode having a ring portion arranged at a position where the opening plane of the inner opening of the ring portion partitions the space between the primary ion generation area and the spray area; and a voltage supplier for applying a predetermined DC voltage to the ring electrode.

In this configuration, the primary ions generated in the primary ion generation area by corona discharge move through the large opening of the ring electrode into the spray area.

In order for the sample-component-derived ions generated within a space near the spray area to be efficiently introduced into the drift region, the ion mobility spectrometer according to the present invention may further include a target-ion-driving electric field creator for creating, within a space between the spray area and an entrance of the drift region, an electric field for driving a sample-component-derived ion toward the entrance of the drift region.

For example, the target-ion-driving electric field creator may include a plurality of ring electrodes and a voltage supplier for applying a predetermined DC voltage to each of the ring electrodes. As another example, the target-ion-driving electric field creator may include a tubular electrical resistor and a voltage supplier for applying a predetermined DC voltage to each of the two ends of the electrical resistor.

In any of these configurations, an electric field in which ions smoothly move from the spray area toward the entrance of the drift region is created. In an ion mobility spectrometer, a stream of neutral gas (which is normally an inert gas) is normally passed through the drift region in the opposite direction to the travelling direction of the ions. Even when such a gas stream is overflowing beyond the entrance of the drift region toward the spray area, the sample-componentderived ions generated within the spray area can be conveyed to the entrance of the drift region, against the gas stream, by the effect of the electric field. In this manner, the sample-component-derived ions generated in a space near the spray area can be efficiently introduced into the drift region and used for an analysis.

In the ion mobility spectrometer according to the present invention, it is preferable to maximally promote the vaporization of the solvent from the micro-droplets formed by the spraying process into the ionization chamber. Within the drift region, a stream of heated neutral gas is supplied from the rear to the front end of the drift region to promote the desolvation. In addition to this, the ion mobility spectrometer may include: a heater for heating the ionization chamber; and a gas introduction section for introducing a heated gas into a space between the ionization chamber and the drift region, and a stream of the heated gas introduced by the gas introduction section is created from the entrance of the drift region toward the spray area.

In this configuration, the micro-droplets are exposed to the dry heated gas within the ionization chamber. Therefore, as compared to the case where the droplets are present in a simple high-temperature atmosphere, the vaporization of the solvent is further promoted, whereby the generation of the target ion originating from the sample is also promoted.

In some cases, the process of spraying the liquid sample into the ionization chamber can be satisfactorily performed by simply spraying the liquid sample. However, in most cases, nebulizer gas is used to assist the spraying process. Accordingly, commonly used sample spray sections include a nebulizer gas tube for ejecting nebulizer gas. With the help of this nebulizer gas ejected from the nebulizer gas tube, the liquid sample is broken into fine droplets and sprayed into the ionization chamber. As a result of various studies, the present inventors have discovered that a vibration due to the nebulizer gas constitutes a major cause of the baseline fluctuation which occurs in a spectrum obtained with an ion mobility spectrometer employing an APCI, ESI or similar type of ion source.

More specifically, if a faint vibration which accompanies the ejection of the nebulizer gas is transmitted to a drift tube within which the drift region is formed, a vibration current occurs in the detector located at the rear end of the drift tube. There are also other elements which simultaneously undergo the vibration, such as a grid electrode which is normally provided in front of the detector in order to reduce an image current induced in the detector by the ions flying into the detector while being drifted, a preamplifier which amplifies the signals obtained with the detector, and a signal cable which connects the detector and the preamplifier. If an electric capacitance (electrostatic capacitance) changes due to such a vibration, an electric current corresponding to that change occurs, which will be detected as a baseline fluctuation in the spectrum. Accordingly, in order to reduce the baseline fluctuation attributable to this factor, it is effective to directly prevent the occurrence of the vibration due to the ejection of the nebulizer gas or check the transmission of this vibration to the drift tube.

Accordingly, in a more preferable mode of the ion mobility spectrometer according to the present invention, an ion chamber forming the ionization chamber and a drift tube having the drift region formed inside are provided as separate bodies, and the ion chamber and the drift tube are fixed individually and independently. The ion chamber and the drift tube may be constructed in a simply contactless form.

It is also possible to connect the ion chamber and the drift tube via an elastic member having the vibration-dampening effect.

In this configuration, even when the amount of nebulizer gas in the APCI ion source is increased and the vibration due to the ejection of the gas is consequently increased, the baseline fluctuation due to the vibration will not occur since the vibration is prevented from reaching the drift tube. That is to say, the aforementioned second objective can be achieved.

Nebulizer gas is commonly used, not only in the APCI ion source but also in other types of atmospheric pressure ion sources, such as the ESI ion source. In practice, the problem of the baseline fluctuation which occurs in a spectrum has also been recognized in other ion mobility spectrometers that employ atmospheric pressure ion sources different from the APCI ion source. Therefore, the aforementioned preferable mode is also useful in an ion mobility spectrometer which employs a different type of atmospheric pressure ion source.

Accordingly, an ion mobility spectrometer according to the second aspect of the present invention developed for achieving the aforementioned second objective is an ion mobility spectrometer in which a liquid sample to be analyzed is sprayed into an ionization chamber maintained at substantially atmospheric pressure, a component in the sample is ionized within the ionization chamber, and the produced ions are transferred to a drift region maintained at substantially atmospheric pressure as well as made to drift through the drift region so as to separate the ions according to their ion mobility, the ion mobility spectrometer characterized in that:

an ion chamber forming the ionization chamber and a drift tube having the drift region formed inside are provided as separate bodies, and the ion chamber and the drift tube are fixed individually and independently.

According to the second aspect of the ion mobility spectrometer, which is an ion mobility spectrometer employing an atmospheric pressure ion source configured to spray a liquid sample into an ionization chamber using nebulizer gas, the vibration due to the ejection of the nebulizer gas is prevented from reaching the drift tube, so that the baseline fluctuation in the spectrum due to the vibration will not occur.

Advantageous Effects of the Invention

The ion mobility spectrometer according to the present invention can produce target ions originating from a sample by effectively using the primary ions generated by corona discharge while preventing sample droplets with insufficient vaporization of the solvent from adhering to the needle electrode for corona discharge. As a result, no spike noise due to an extinction of the corona discharge or due to a sudden surge of the discharge occurs in the spectrum, so that a high-quality spectrum reflecting the ions produced in a stable manner can be obtained.

In the ion mobility spectrometer according to the second aspect of the present invention, even when the supply of the nebulizer gas is increased, the baseline fluctuation in the spectrum is effectively suppressed, so that a highly accurate spectrum can be obtained.

DESCRIPTION OF EMBODIMENTS

Several embodiments of the ion mobility spectrometer according to the present invention will be described with reference to the attached drawings.

First Embodiment

Figure 1:
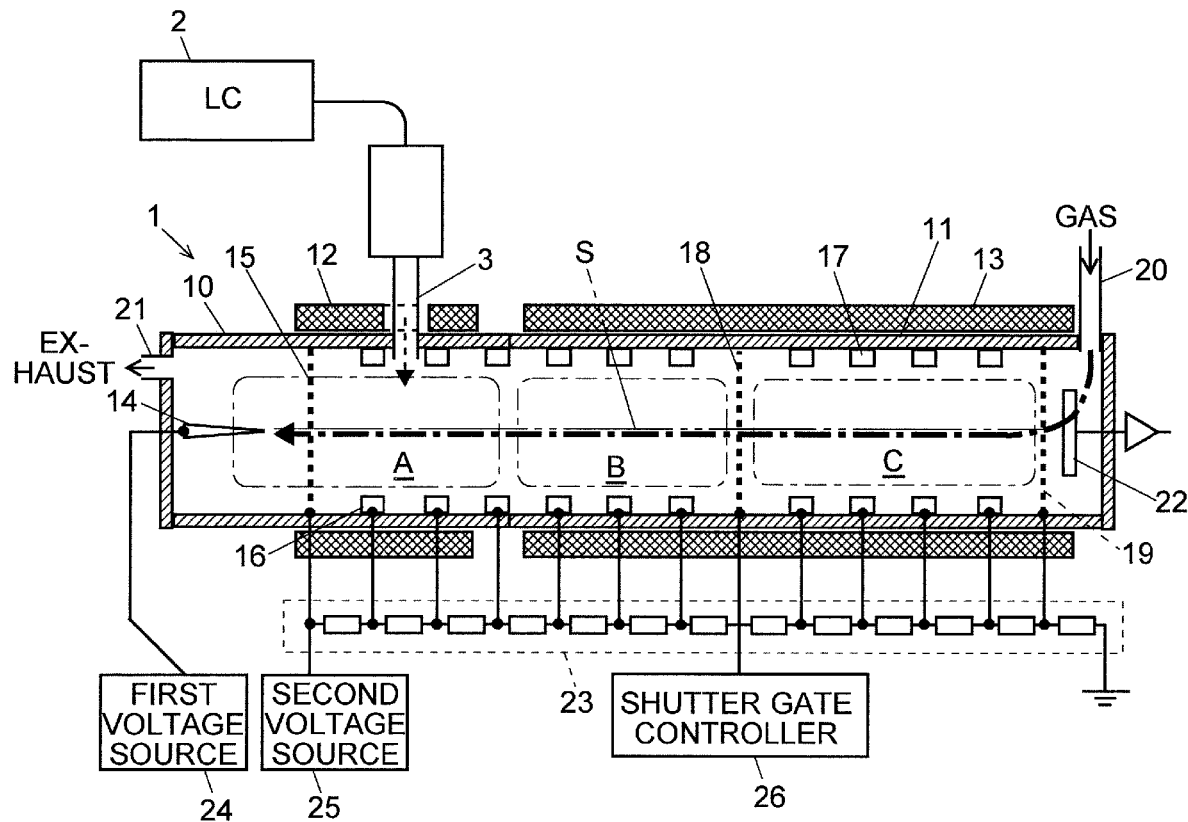
FIG. 1 is a schematic configuration diagram of an LC-APCI-IMS device according to the first embodiment of the present invention.
Figure 2:
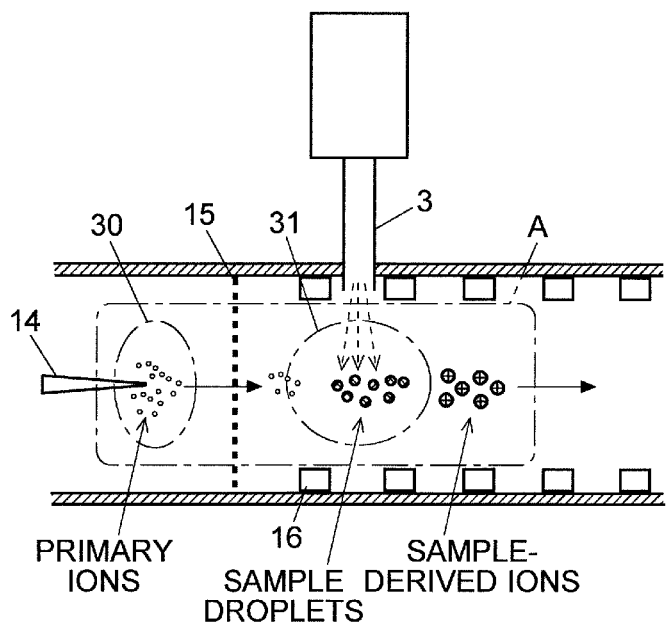
FIG. 2 is a schematic configuration diagram of the APCI ion source and surrounding elements in FIG. 1.

FIG. 1 is a schematic configuration diagram of a liquid chromatograph atmospheric pressure chemical ionization source ion mobility spectrometer (LC-APCI-IMS device) according to the first embodiment of the present invention. FIG. 2 is a schematic configuration diagram of the APCI ion source and surrounding elements in FIG. 1.

This LC-APCI-IMS device is roughly divided into an LC unit 2 and APCI-IMS unit 1. Though not shown, the LC unit 2 is provided with a mobile phase supplier including a liquid-sending pump, an injector for introducing a sample into a mobile phase, a column for separating the components in a sample, and other elements, whereby a plurality of components contained in a sample are temporally separated. A liquid sample containing the separated components is continuously supplied to the APCI-IMS unit 1.

The APCI-IMS unit 1 is provided with an ion chamber 10 with the inner space forming an ionization chamber for ionizing the components in a sample, and a drift tube 11 with the inner space forming the drift region for separating ions by using their ion mobility. In the present embodiment, the ion chamber 10 and drift tube 11 are combined into a single body having a substantially cylindrical shape with a uniform diameter. The ion chamber 10 and drift tube 11 are circumferentially provided with heating blocks 12 and 13 for respectively heating them.

In the circumferential wall of the ion chamber 10, an APCI spray nozzle 3 is attached in such a manner that the spraying direction of the liquid sample is substantially orthogonal to the central axis of the ion chamber 10. The central axis of the ion chamber 10 and that of the drift tube 11 coincide with each other. These axes are hereinafter simply referred to as the "central axis S".

The spray nozzle 3, which is supplied with a liquid sample from the LC unit 2, serves to make this sample carried by a stream of nebulizer gas (which is normally an inert gas, such as nitrogen or helium) and sprayed into the ion chamber 10 through a drying tube heated to high temperatures (300-500° C.). Within the ion chamber 10, a needle electrode 14 for inducing corona discharge is provided at the end which is opposite to the end leading to the drift tube 11, and a first grid electrode 15 having a large number of openings is stretched across the space between this needle electrode 14 and the spray nozzle 3. Between this first grid electrode 15 and the drift tube 11, a plurality of ring electrodes 16 are arranged at predetermined intervals along the extending direction of the central axis S.

A plurality of ring electrodes 17 are similarly arranged within the drift tube 11 at predetermined intervals along the extending direction of the central axis S, forming a continuation of the ring electrodes 16 in the ion chamber 10. It should be noted that a shutter gate 18 (which is a grid electrode) is provided in place of the ring electrode 17 at a predetermined position in the middle of the drift tube 11. Within the drift tube 11, an ion detector 22 is placed at the end which is opposite to the end leading to the ion chamber 10, along with a second grid electrode 19 stretched across the space between this ion detector 22 and the rearmost ring electrode 17. A gas introduction tube 20 is connected to the circumferential wall of the drift tube 11 at a point near the ion detector 22. Through this gas introduction tube 20, neutral gas (e.g. nitrogen gas) is supplied into the drift tube 11 at a constant flow rate. As indicated by the thick chained line in FIG. 1, the neutral gas supplied into the drift tube 11 flows in the direction from the ion detector 22 to the needle electrode 14, to be discharged through the exhaust port 21 provided at the end of the ion chamber 10. The neutral gas passed through the drift tube 11 is normally heated to approximately the same temperature as the drift tube 11 (around 200° C.) before being introduced into the tube.

The first grid electrode 15, plurality of ring electrodes 16 and 17 as well as second grid electrode 19 are individually connected to a voltage-dividing circuit 23 formed by an array of resistors. The voltage-dividing circuit 23 generates different levels of DC voltages by dividing a predetermined amount of DC voltage generated by a second voltage source 25, and those DC voltages are respectively applied to the aforementioned electrodes. Additionally, a high voltage of approximately a few kV for corona discharge is applied from a first voltage source 24 to the needle electrode 14, while a control voltage for controlling the passage and blockage of ions is applied from a shutter gate controller 26 to the shutter gate 18. The first voltage source 24, second voltage source 25 and shutter gate controller 26 are controlled by a control unit (not shown).

In the LC-APCI-IMS device of the present embodiment, the region labeled "A" within the ion chamber 10 in FIG. 1 is the ionization region, the one labeled "B" within the drift tube 11 is the desolvation region, and the one labeled "C" within the same drift tube 11 is the drift region. In other words, a desolvation region B for promoting the solvent vaporization for the sample-derived target ions (the ions contained in micro-droplets) from which the solvent has been insufficiently vaporized is provided between the ionization region A for ionizing the target components and the drift region C for separating and detecting the ions.

An operation for analyzing an ion originating from a target component in a sample in the LC-APCI-IMS device of the present embodiment is hereinafter described.

When a liquid sample containing the compounds separated by the LC unit 2 reaches the APCI spray nozzle 3, the liquid sample is broken into micro-droplets and sprayed into the ionization chamber with the help of the nebulizer gas. Since the ion chamber 10 is heated to appropriate temperatures (normally, 150-300° C.) by the heating block 12, the solvent contained in the micro-droplets is vaporized and the target components in the sample turn into gas molecules. Meanwhile, the high voltage applied from the first voltage source 24 to the needle electrode 14 creates an electric field concentrated at the tip of the thin needle electrode 14. Since the distance between the tip of the needle electrode 14 and the first grid electrode 15 is as short as a few to ten millimeters along the central axis S, a corona discharge occurs due to the non-uniform electric field formed between the tip of the needle electrode 14 and the first grid electrode 15. This corona discharge ionizes the air around the tip of the needle electrode 14, neutral gas coming from the drift tube 11 and other substances, whereby primary ions are generated.

As shown in FIG. 2, the primary ions are mostly generated within a primary ion generation area 30 around the tip of the needle electrode 14. The primary ion generation area 30 is separated from a spray area 31 in which a large number of droplets sprayed from the APCI spray nozzle 3 are present. Within the space between these two areas 30 and 31, an electric field is created due to the DC voltages applied to the first grid electrode 15 and the ring electrodes 16. This electric field has a potential gradient which drives the primary ions along the central axis S toward the spray area 31. Due to the effect of this electric field, the primary ions existing in the primary ion generation area 30 pass through the openings of the first grid electrode 15 and move toward the spray area 31. Upon reaching a space near the spray area 31, the primary ions react with the sample components gasified from or contained in the droplets, whereby ions originating from those components are produced.

In this manner, despite the spatial separation between the primary ion generation area 30 and the spray area 31, sample-component-derived ions can be efficiently produced in a space near the spray area 31. Due to the sufficient separation between the needle electrode 14 and the spray area 31 as well as the presence of the grid electrode 15 between them, the sample droplets cannot reach an area near the tip of the needle electrode 14. In this manner, the adhesion of the sample droplets to the needle electrode 14 is prevented, so that the corona discharge can be induced in a stable state by the previously set application voltage.

The polarity of the sample-component-derived target ions to be eventually generated depends on that of the primary ions, while the polarity of the primary ions is determined by that of the voltage applied to the needle electrode 14. Accordingly, the polarity of the voltage applied from the first voltage source 24 to the needle electrode 14 should be changed according to the polarity of the target ion to be analyzed. The polarity of the voltage generated by the second voltage source 25 should also be changed accordingly.

The target ions generated in a space near the spray area 31 move toward the shutter gate 18 under the effect of the electric field created by the voltages applied to the ring electrodes 16 and 17. The ions generated in the spray area 31 include not only the gas-phase target ions but also target ions which exist inside the droplets from which the solvent has incompletely vaporized. The latter ions effectively act as electrically charged droplets and move toward the shutter gate 18 along with the gas-phase target ions under the effect of the electric field. The drift tube 11 is heated to appropriate temperatures (normally, 150-250° C.) by the heating block 13. The high-temperature neutral gas introduced from the gas introduction tube 20 and flowing through the drift region C passes through the desolvation region B between the space near the entrance end of the drift tube 11 and the shutter gate 18. Therefore, when passing through this desolvation region B, the charged droplets are exposed to the high-temperature neutral gas, whereby the vaporization of the solvent is further promoted and the target ions in the droplets also turn into the gas phase.

Depending to the voltage applied from the shutter-gate controller 26, the shutter gate 18 periodically repeats the "open" state for allowing the passage of the ions and the "closed" state for blocking the passage of the ions. The period of time during which the shutter gate 18 is in the open state is sufficiently shorter than the drift time required for target ions to reach the detector 22 after passing through the shutter gate 18. Accordingly, the timing at which the shutter gate 18 is in the open state is used as the starting point to measure the drift time.

A typical example of the shutter gate 18 is the so-called "BN (Bradbury-Nielsen) gate". It has the line-and-space structure having thin metallic wires with a thickness of approximately 100 μm stretched at intervals of several hundred μm. When all neighboring metallic wires are at the same potential, the shutter gate 18 is in the open state. When voltages which create a potential difference of approximately 100 V between the neighboring metallic wires are applied, the shutter gate 18 is in the closed state.

If insufficiently desolvated droplets were allowed to reach the shutter gate 18 and adhere to its metallic wires, unwanted electric discharge might occur between the neighboring metallic wires, causing damage to those metallic wires. The present ion mobility spectrometer prevents such a situation by performing sufficient desolvation within the desolvation region B before the shutter gate 18, as described earlier, so as to prevent the droplets from reaching the shutter gate 18.

The electric field created within the desolvation region B has a potential gradient which forms a downward slope for the target ions to move toward the shutter gate 18. Therefore, when the shutter gate 18 is closed, the target ions which have reached the shutter gate 18 stay at the gate or become diffused. Then, when the shutter gate 18 is opened for a short period of time, the staying target ions simultaneously pass through the shutter gate 18 and enter the drift region C. While drifting through the drift region C, those ions are separated according to their ion mobility and reach the detector 22 through the second grid electrode 19. The detector 22 produces detection signals corresponding to the amount of arriving ions and sends those signals to an external system. The second grid electrode 19 serves to prevent an image current from being induced in the detector 22 due to the motion of the ions in the vicinity of the detector 22. Preventing the occurrence of the image current has the effect of improving the rising characteristic of the detection signal which is generated when a target ion arrives at the detector 22.

As described thus far, the ion mobility spectrometer of the first embodiment can achieve a high level of ion generation efficiency while maintaining a stable generation of the corona discharge by preventing the adhesion to the needle electrode 14 of the droplets formed by the spraying process from the APCI spray nozzle 3.

Second Embodiment

Figure 3:
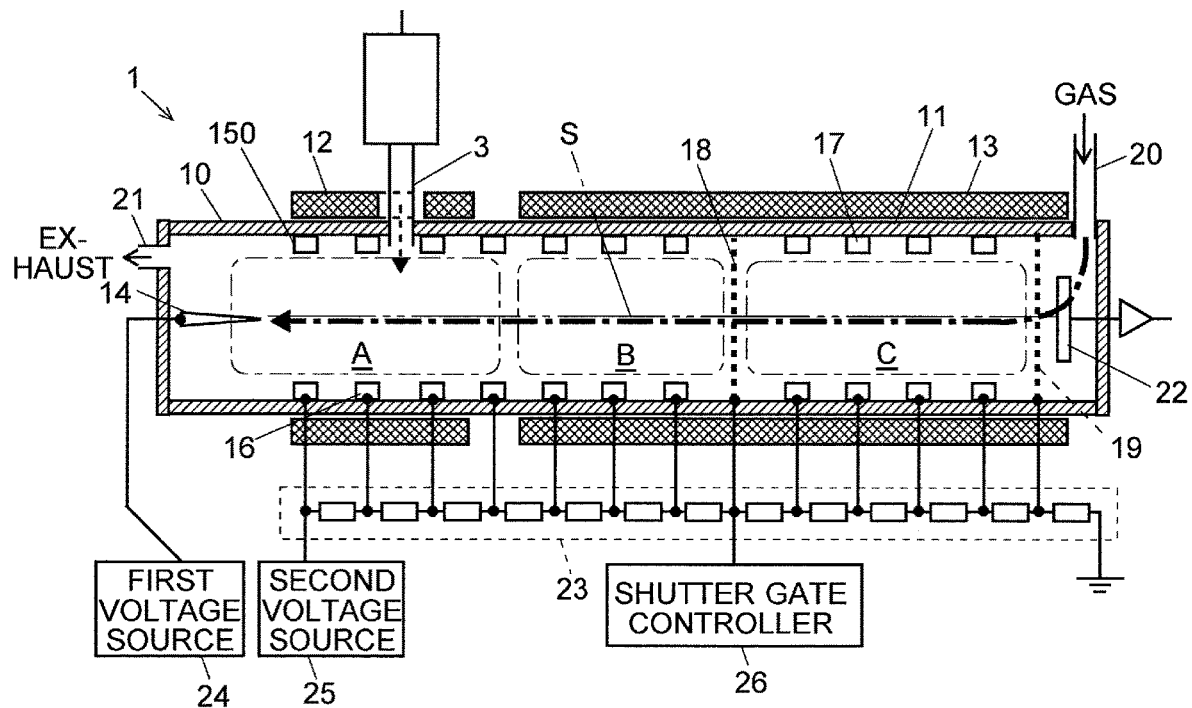
FIG. 3 is a schematic configuration diagram of an LC-APCI-IMS device according to the second embodiment of the present invention.

FIG. 3 is a schematic configuration diagram of an LC-APCI-IMS device according to the second embodiment of the present invention. The same components as used in the LC-APCI-IMS device according to the first embodiment shown in FIG. 1 are denoted by the same numerals.

In the LC-APCI-IMS device of the second embodiment, a ring electrode 150 similar to the ring electrodes 16 is provided in place of the first grid electrode 15 in the LC-APCI-IMS device of the first embodiment. The ring electrode 150 can similarly form an almost flat equipotential surface within the inner space of its ring portion. The ring electrode 150 also functions as the counter-electrode for the needle electrode 14.

Third Embodiment

Figure 4:
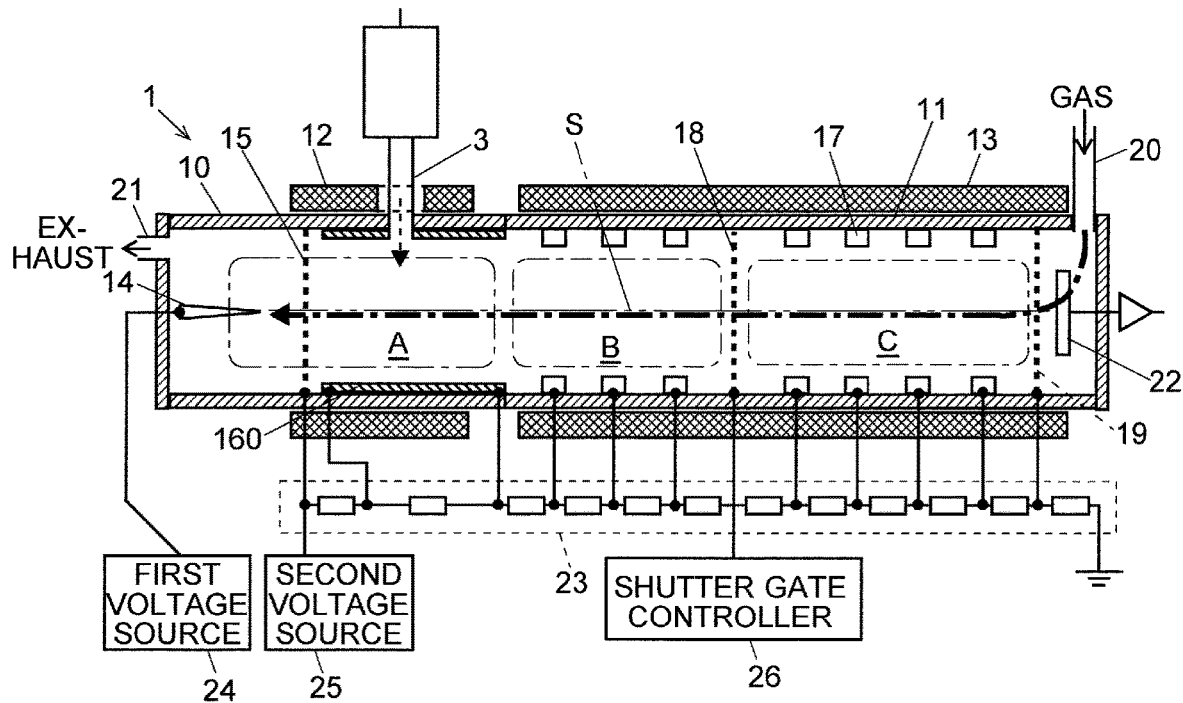
FIG. 4 is a schematic configuration diagram of an LC-APCI-IMS device according to the third embodiment of the present invention.

FIG. 4 is a schematic configuration diagram of an LC-APCI-IMS device according to the third embodiment of the present invention. The same components as used in the LC-APCI-IMS device according to the first embodiment shown in FIG. 1 are denoted by the same numerals.

In the LC-APCI-IMS device of the third embodiment, in place of the ring electrodes 16 in the LC-APCI-IMS device of the first embodiment, an electrical resistor 160 having a cylindrical shape is provided along the inner circumferential wall of the ion chamber 10, with two predetermined voltages applied from the voltage-dividing circuit 23 to the two ends of the electrical resistor 160, respectively. In order to eliminate the potential difference in the circumferential direction, it is preferable to attach an annular electric conductor to each end of the electrical resistor 160 and apply the aforementioned voltages to those electric conductors. Within the inner space of the electrical resistor 160, an electric field having a linear potential gradient along the central axis S is created. Due to the effect of this electric field, the primary ions generated in a space near the needle electrode 14 are driven toward a space near the spray area. Furthermore, the target ions generated in a space near the spray area are driven toward the entrance end of the drift tube 11.

Fourth Embodiment

Figure 5:
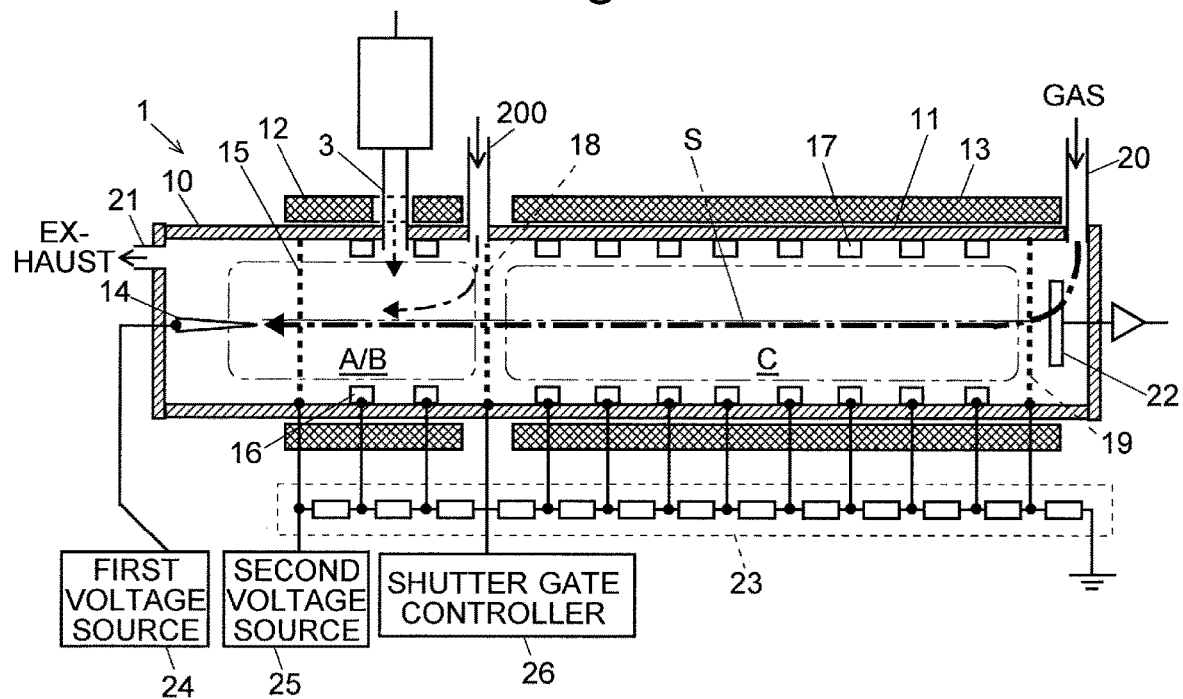
FIG. 5 is a schematic configuration diagram of an LC-APCI-IMS device according to the fourth embodiment of the present invention.

FIG. 5 is a schematic configuration diagram of an LC-APCI-IMS device according to the fourth embodiment of the present invention. The same components as used in the LC-APCI-IMS device according to the first embodiment shown in FIG. 1 are denoted by the same numerals.

In the LC-APCI-IMS device of the fourth embodiment, in order to improve the ion separation performance, the drift region C is elongated by placing the shutter gate 18 at the entrance of the drift tube 11. However, for this arrangement, the idea of providing the desolvation region within the drift tube 11 is abandoned. Therefore, it is necessary to even further promote the desolvation within the limited space of the ion chamber 10. To this end, dry gas is supplied into the ion chamber 10 through a dry gas introduction tube 200 whose outlet end is located between the ion chamber 10 and the drift tube 11. Additionally, the temperature of the heating block 12 surrounding the ion chamber 10 is set at a higher level than the temperature of the heating block 13 surrounding the drift tube 11. By such a system, the vaporization of the solvent from the droplets in the ion chamber 10 is further promoted, so that the situation in which the droplets reach the shutter gate 18 can be avoided despite the shortened distance between the spray area and the shutter gate 18.

Fifth Embodiment

Figure 6:
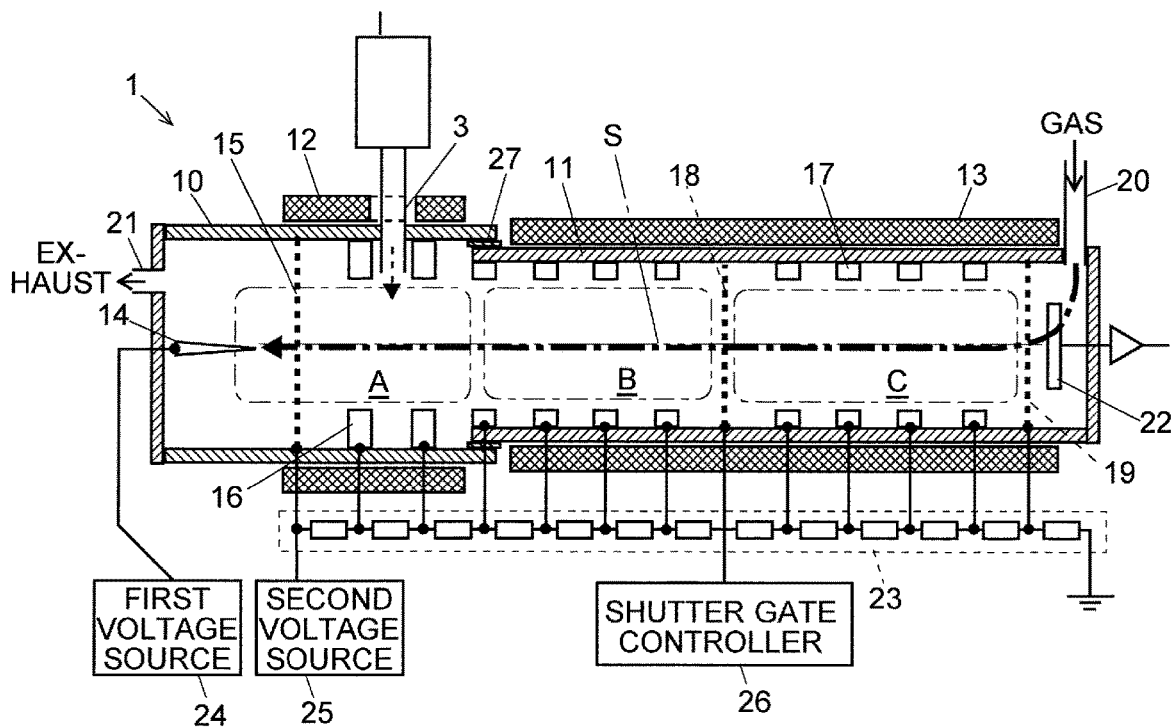
FIG. 6 is a schematic configuration diagram of an LC-APCI-IMS device according to the fifth embodiment of the present invention.

FIG. 6 is a schematic configuration diagram of an LC-APCI-IMS device according to the fifth embodiment of the present invention. The same components as used in the LC-APCI-IMS device according to the first embodiment shown in FIG. 1 are denoted by the same numerals. Unlike the LC-APCI-IMS device of the first embodiment in which the ion chamber 10 and the drift tube 11 are combined into a single body, the ion chamber 10 and the drift tube 11 in the LC-APCI-IMS device of the fifth embodiment are constructed as separated bodies, which are individually and independently held by fixation members (not shown) within the casing of the device. Although the gap between the ion chamber 10 and the drift tube 11 is narrow, a vibration isolator 27 is provided in this gap to prevent external air and/or suspended matters from entering the ion chamber 10 through the gap. By such a construction, the vibration of the ion chamber 10 is prevented from reaching the drift tube 11.

As noted earlier, in the case of spraying a liquid sample using nebulizer gas in the APCI spray nozzle 3, a faint vibration occurs in the ion chamber 10 due to the spraying action. If this vibration were allowed to reach the drift tube 11, the vibration would constitute a factor of the baseline fluctuation in the spectrum. However, in the LC-APCI-IMS device of the present embodiment, even when a faint vibration occurs in the ion chamber 10, the baseline fluctuation due to such a vibration will not occur since the vibration cannot reach the drift tube 11. Needless to say, if the entry of external air or other substances through the gap between the ion chamber 10 and the drift tube 11 does not cause any problem, the vibration isolator 27 for closing the gap is unnecessary.

Such a problem is not limited to the APCI ion source; a similar problem can occur in any atmospheric pressure ion source constructed to spray a liquid sample into an ionization chamber by using nebulizer gas, such as the ESI ion source or APPI ion source. Accordingly, the structure in which the ion chamber 10 and the drift tube 11 are independently held as separate bodies as shown in FIG. 6 can also be applied in an ion mobility spectrometer employing an atmospheric pressure ion source different from the APCI ion source, as will be hereinafter described.

Sixth Embodiment

Figure 7:
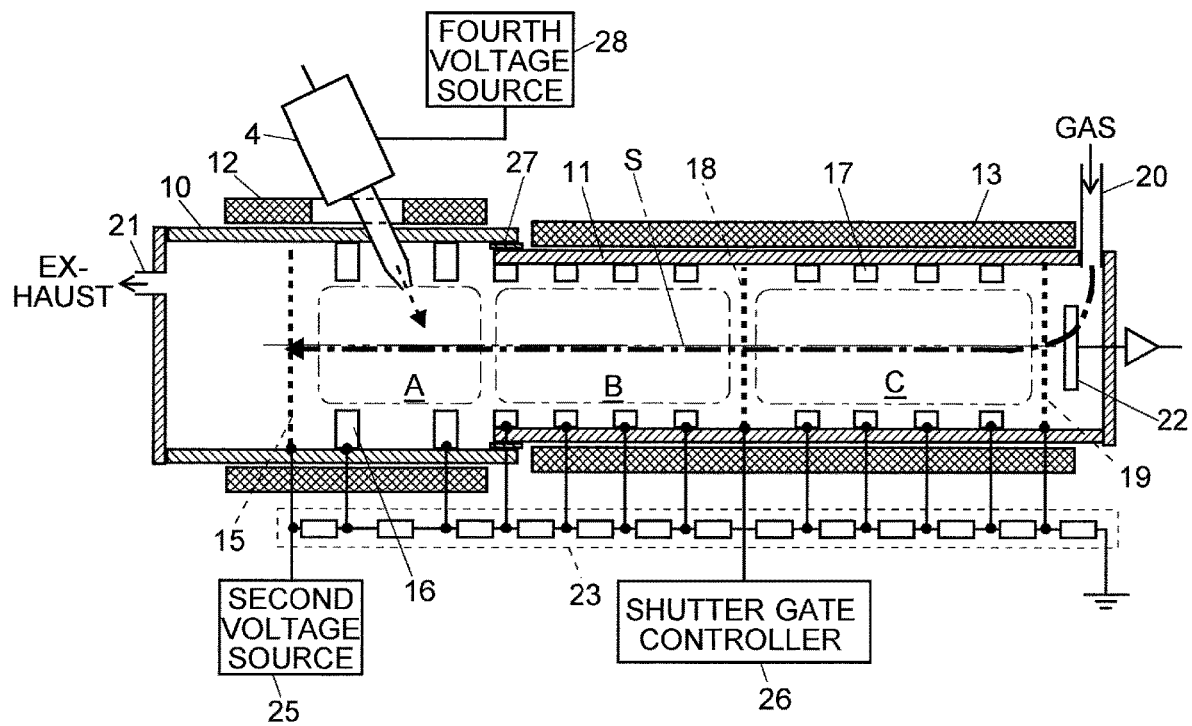
FIG. 7 is a schematic configuration diagram of an LC-ESI-IMS device according to the sixth embodiment of the present invention.

FIG. 7 is a schematic configuration diagram of one embodiment of an LC-ESI-IMS device obtained by changing the ion source in the LC-APCI-IMS device of the fifth embodiment to an ESI ion source. The same components as used in the LC-APCI-IMS device according to the fifth embodiment shown in FIG. 6 are denoted by the same numerals.

In the LC-ESI-IMS device of the sixth embodiment, an ESI spray nozzle 4 is attached to the circumferential wall of the ion chamber 10 in place of the APCI spray nozzle. A liquid sample which has reached the ESI spray nozzle 4 is transformed into electrically charged droplets by being sprayed through a non-uniform electric field created by the high voltage applied from a fourth voltage source 28 to the spray nozzle 4. The charged droplets become even finer particles by coming in contact with neutral gas (or similar gas). Concurrently, the solvent is vaporized by heat. Through such a process, gas-phase target ions are generated.

It should be noted that the spraying direction of the liquid sample from the ESI spray nozzle 4 is not orthogonal to the central axis S but obliquely directed toward the shutter gate 18 at a certain angle to the central axis S. This is intended to help the charged droplets and the target ions produced from those droplets travel toward the shutter gate 18.

Similarly to the fifth embodiment, the ion chamber 10 and the drift tube 11 in the sixth embodiment are constructed as separate bodies and held independently. Therefore, the faint vibration which occurs in the ion chamber 10 cannot reach the drift tube 11, so that the baseline fluctuation in the spectrum due to the vibration of the drift tube 11 will not occur.

Seventh Embodiment

Figure 8:
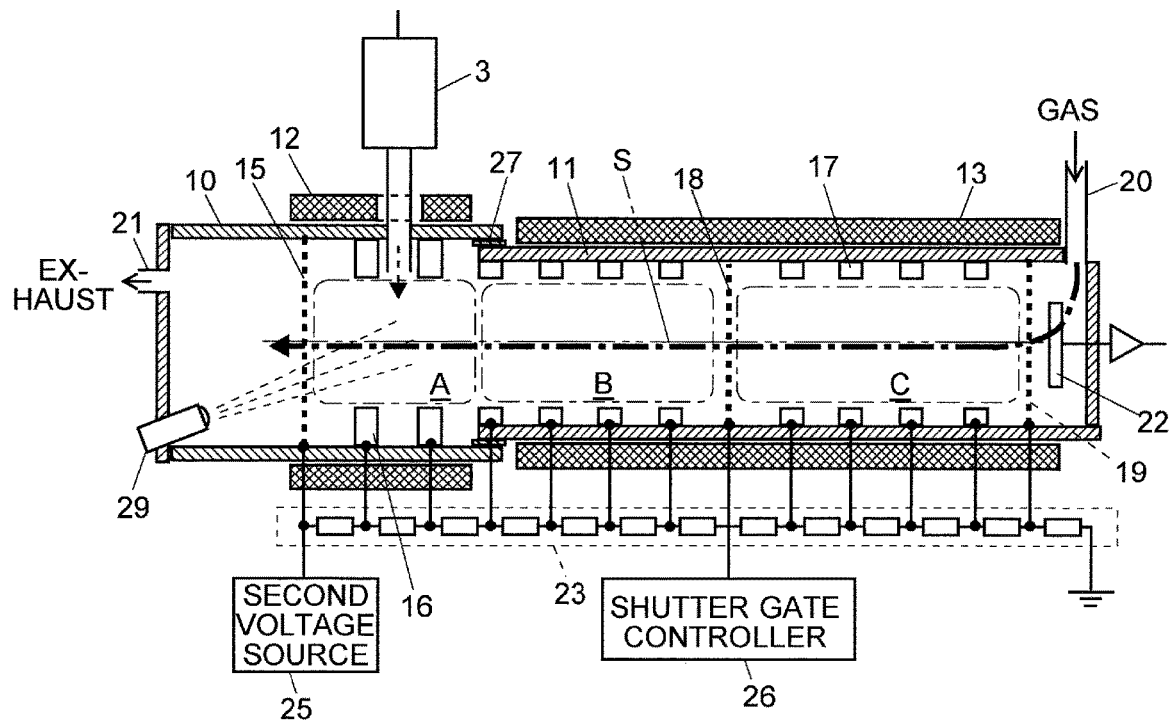
FIG. 8 is a schematic configuration diagram of an LC-APPI-IMS device according to the seventh embodiment of the present invention.
Figure 9:
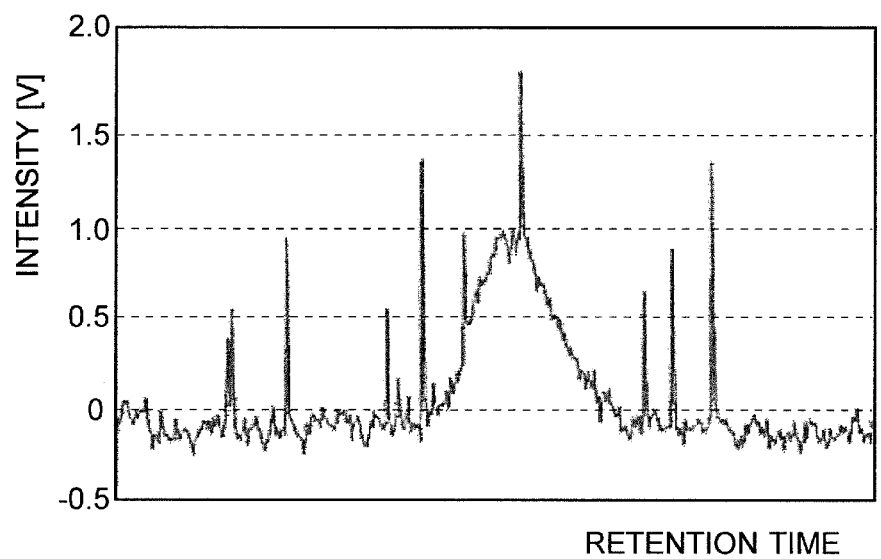
FIG. 9 is a graph showing one example of the chromatograph chromatogram observed with a conventional LC-APCI-IMS device in which spike noises are present.
Figure 10:
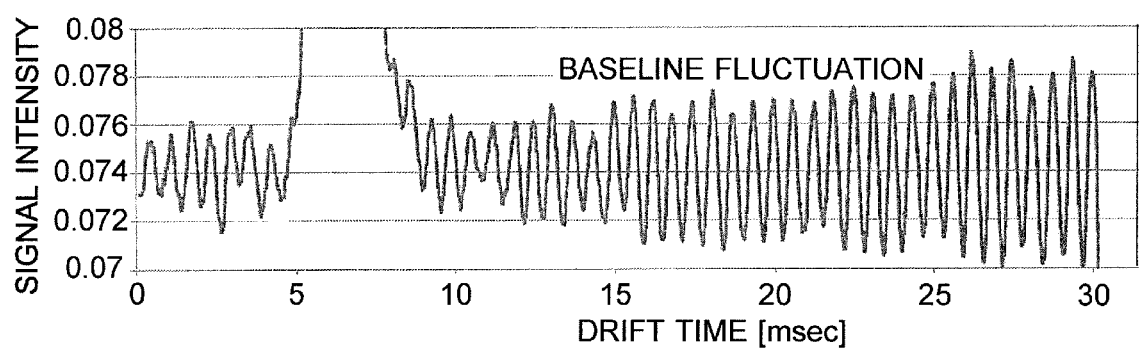
FIG. 10 is a graph showing an example of the spectrum (IMS spectrum) observed with a conventional LC-APCI-IMS device in which the baseline fluctuation is present.

FIG. 8 is a schematic configuration diagram of one embodiment of an LC-APPI-IMS device obtained by changing the ion source in the LC-APCI-IMS device of the fifth embodiment to an APPI ion source. The same components as used in the LC-APCI-IMS device according to the fifth embodiment shown in FIG. 6 are denoted by the same numerals.

In the LC-APPI-IMS device of the seventh embodiment, an APPI light source 29 is provided within the ion chamber 10. The APPI light source 29 is arranged so that the emitted light illuminates a space near the spray area in which a large number of droplets sprayed from the spray nozzle 3 are present. Sample components are ionized by the effect of this light.

Similarly to the fifth embodiment, the ion chamber 10 and the drift tube 11 in the seventh embodiment are constructed as separate bodies and held independently. Therefore, the faint vibration which occurs in the ion chamber 10 cannot reach the drift tube 11, so that the baseline fluctuation in the spectrum due to the vibration of the drift tube 11 will not occur.

It should be noted that any of the previous embodiments is a mere example of the present invention, and any change, modification or addition appropriately made within the spirit of the present invention will naturally fall within the scope of claims of the present application.

REFERENCE SIGNS LIST

1 . . . APCI-IMS Unit
2 . . . LC Unit
3 . . . APCI Spray Nozzle
4 . . . ESI Spray Nozzle
10 . . . Ion Chamber
11 . . . Drift Tube
12, 13 . . . Hearting Block
14 . . . Needle Electrode
15 . . . First Grid Electrode
16, 17, 150 . . . Ring Electrode
18 . . . Shutter Gate
19 . . . Second Grid Electrode
20 . . . Gas Introduction Tube
21 . . . Exhaust Port
22 . . . Ion Detector
23 . . . Voltage-Dividing Circuit
24 . . . First Voltage Source
25 . . . Second Voltage Source
26 . . . Shutter Gate Controller
27 . . . Vibration Isolator
28 . . . Fourth Voltage Source
160 . . . Electrical Resistor
200 . . . Dry Gas Introduction Tube
A . . . Ionization Region
B . . . Desolvation Region
C . . . Drift Region

The invention claimed is:

1. An ion mobility spectrometer in which a component in a sample is ionized within an ionization chamber maintained at atmospheric pressure and target ions are introduced into and made to drift through a drift region maintained at atmospheric pressure so as to separate the ions according to their ion mobility, the ion mobility spectrometer comprising:
   a) a sample spray area for spraying a liquid sample to be analyzed into the ionization chamber;
   b) a primary ion generation area located at one side of the sample spray area and comprising a needle electrode for inducing corona discharge to generate a primary ion;
   c) a primary-ion-driving electric field creator for creating, between the sample spray area and the primary ion generation area, an electric field for driving the generated primary ion from the primary ion generation area toward the sample spray area, and causing the primary ion to react with the liquid sample to generate a sample-component-derived target ion and drift to the drift area, the drift area being located at another side of the sample spray area opposite to the primary ion generation area; and
   d) a gas supply section connected to the drift area and supplying a stream of neutral gas to pass through the drift region, the sample spray area, and the primary ion generation area, in that order.

2. The ion mobility spectrometer according to claim 1, wherein:
   the primary-ion-driving electric field creator comprises: a grid electrode facing the needle electrode, the grid electrode arranged so as to partition a space between the primary ion generation area and the sample spray area; and a voltage supplier for applying a predetermined DC voltage to the grid electrode.

3. The ion mobility spectrometer according to claim 1, wherein:
   the primary-ion-driving electric field creator comprises: a ring electrode having a ring portion arranged at a position where an opening plane of an inner opening of the ring portion partitions a space between the primary ion generation area and the sample spray area; and a voltage supplier for applying a predetermined DC voltage to the ring electrode.

4. The ion mobility spectrometer according to claim 1, further comprising:
   a target-ion-driving electric field creator for creating, within a space between the sample spray area and an entrance of the drift region, an electric field for driving the sample-component-derived target ion toward an entrance of the drift region.

5. The ion mobility spectrometer according to claim 4, wherein:
   the target-ion-driving electric field creator comprises: a plurality of ring electrodes; and a voltage supplier for applying a predetermined DC voltage to each of the ring electrodes.

6. The ion mobility spectrometer according to claim 4, wherein:
   the target-ion-driving electric field creator comprises: a tubular electrical resistor; and a voltage supplier for applying a predetermined DC voltage to each of two ends of the electrical resistor.

7. The ion mobility spectrometer according to claim 1, wherein:
   a gas introduction section for introducing a heated gas into a space between the ionization chamber and the drift region is further provided, and a stream of heated gas introduced by the gas introduction section is created from an entrance of the drift region toward the sample spray area.

8. The ion mobility spectrometer according to claim 1, wherein:

an ion chamber forming the ionization chamber and a drift tube having the drift region formed inside are provided as separate bodies, and the ion chamber and the drift tube are fixed individually and independently.

\* \* \* \* \*